US005821092A

United States Patent [19]
Nagarajan et al.

[11] Patent Number: 5,821,092
[45] Date of Patent: Oct. 13, 1998

[54] PRODUCTION OF 1,3-PROPANEDIOL FROM GLYCEROL BY RECOMBINANT BACTERIA EXPRESSING RECOMBINANT DIOL DEHYDRATASE

[75] Inventors: Vasantha Nagarajan, Wilmington; Charles Edwin Nakamura, Claymont, both of Del.

[73] Assignee: E. I. du Pont de Nemours and Company, Wilmington, Del.

[21] Appl. No.: 687,852

[22] Filed: Jul. 26, 1996

Related U.S. Application Data

[62] Division of Ser. No. 440,377, May 12, 1995, Pat. No. 5,633,362.

[51] Int. Cl.$^6$ ..................................... C12P 7/18
[52] U.S. Cl. ................ 435/158; 435/232; 435/252.3; 435/252.31; 435/252.33; 435/252.35; 435/252.5; 435/252.7; 435/320.1; 536/23.1; 536/23.2; 536/23.7
[58] Field of Search ................... 435/158, 842, 435/252.3, 252.33, 232, 252.31, 252.35, 252.5, 252.7, 320.1; 536/23.1, 23.2, 23.7

[56] References Cited

U.S. PATENT DOCUMENTS

| 4,935,554 | 6/1990 | Murphy et al. | 568/867 |
|---|---|---|---|
| 4,962,027 | 10/1990 | Slininger et al. | 435/147 |
| 5,015,789 | 5/1991 | Arntz et al. | 568/862 |
| 5,164,309 | 11/1992 | Gottschalk et al. | 435/158 |
| 5,254,467 | 10/1993 | Kretschmann et al. | 435/158 |

FOREIGN PATENT DOCUMENTS

| WO 93/25696 | 12/1993 | WIPO | C12P 7/18 |

OTHER PUBLICATIONS

J. Bacteriol. (1995), 177(15), 4392–401, Daniel, Rolf et al., "Biochemical and Molecular Characterization of the Oxidative Branch of Glycerol Utilization by Citrobacter Freundii".

J. Bacteriol., vol. 177, No. 8, 1995, pp. 2151–2156, Daniel, Rolf et al., "Purification of 1,3–Propanediol Dehydrogenase from Citrobacter Freundii and Cloning, Sequencing and Overexpression of the Corresponding Gene in *Escherichia Coli*".

Gene, vol. 85, 1989, pp. 209–214, Paige E. Goodlove et al., "Cloning and Sequence Analysis of the Fermentative Alcohol–Dehydrogenase–Encoding Gene of *Escherichia Coli*".

Daniel et al, *FEMS Microbiol. Lett.*, 100, 281–286 (1992).

Forage, R.G. et al, *Bacteriology*, 149(2), 413–419 (1982).

Jeter, R.M., *J. Gen. Microbiology*, 136, 887–896 (1990).

Tong, I–T et al, *Appl. and Environmental Microbiology*, 57(12), 3541–3546 (1991).

Ichikawa et al, *J. Ferment. Technol.*, 63(2), 135–141 (1985).

Sprenger, G.A. et al, *J. Gen. Microbiology*, 135, 1255–1262 (1989).

Boenigk, R. et al, *Appl. Microbiol. and Biotechnol.*, 38, 453–457 (1993).

Forsberg, C.W., *Appl. Environ. Microbiol.*, 53(4), 639–643 (1987).

Zeng, A–P. et al, *Enzyme Microb. Technol.*, 15, 770–779 (1993).

Bobik, T.A. et al, *J. of Bacteriol.*, 174(7), 2253–2266 (1992).

Hartmanis, M.G.N. et al, *Archives of Biochem. and Biophysics*, 245(1), 144–152 (1986).

Tobimatsu, T. et al, *J. Biol. Chem.*, 270(13), 7142–7148 (1995).

Tong et al. "1,3–Propanediol production by *Escherichia coli* expressing genes from the Klebsiella pneumoniae dha regulon" App. Envirn. Microbiol. 57, 3541–3546 Dec. 1991.

Daniel et al. "Growth temperature–dependent activity of glycerol dehydratase in . . . " FEMS Microbiol. Lett. 100, 281–286 Dec. 1992.

Tobimatsu et al. "Molecular cloning, sequencing, and expression of the genes encoding . . . " J. Biol. Chem. 270, 7142–7148 Mar. 1995.

McGee et al. "Diol dehydrtase: N–terminal amino acid sequence and subunit stochiometry" Biochem. Biophys. Res. Comm. 108, 547–551 Sep. 1982.

*Primary Examiner*—Eric Grimes
*Assistant Examiner*—Nashaat T. Nashed

[57] ABSTRACT

A process is provided for the bioconversion of glycerol to 1,3-propanediol in which genes from a bacteria known to possess a diol dehydratase enzyme for 1,2-propanediol degradation are cloned into a bacterial host and the host is grown in the presence of glycerol; expression of the foreign genes in the host cell facilitates the enzymatic conversion of glycerol to 1,3-propanediol which is isolated from the culture.

10 Claims, 4 Drawing Sheets

```
Klebsiella#    ---->1  MRSKRFEALAKRPVNQDGFVKEWIEEGFIAMESPNDPKPSIRIVNGAVTE  50
                      ||||||||||||||||||||||||||||||||||||||||||:|||||||
Salmonella*    ---->1  MRSKRFEALAKRPVNQDGFVKEWIEEGFIAMESPNDPKPSIKIVNGAVTE  50

51  LDGKPVEQFDLIDHFIARYGINLARAEEVMAMDSVKLANMLCDPNVKRSD  100
                       ||||||.:|
                   51  LDGKPVSEF........................................  59
```

\#      SEQ ID NO.: 3

\*      SEQ ID NO.: 4

```
pduC_Kp #  ---→  1  M.RSKRFEALAKRPVNQDGFVKEWIEEGFIAMESPNDPKPSIRIVNGAVT  49
                    | ||||||.||.|||||||::  ||  |||:||||||  ||  .|:::  ||  :.
dhaB_Cf *  ---→  1  MRRSKRFEVLAQRPVNQDGLIGEWPEEGLIAMESPYDPASSVKVENGRIV  50

50  ELDGKPVEQFDLIDHFIARYGINLARAEEVMAMDSVKLANMLCDPNVKRS  99
                    |||||.  .:||:||:|||  |:||::  ||  .|.:|.:..:|.||.|  :|.|.
                51  ELDGKSRAEFDMIDRFIADYAINVPEAERAMQLDALEIARMLVDIHVSRE  100

100  DIVPLTTAMTPAKIVEVVSHMNVVEMMMAMQKMRARRTPSQQAHVTNIKD  149
                    :|:::|||:||||  :||:.:|||||||||:|||||||||.|.||||:||
               101  EIIAITTAITPAKRLEVMAQMNVVEMMMALQKMRARRTPSNQCHVTNLKD  150

150  NPVQIAADAAEGAWRGFDEQETTVAVARYAPFNAIALLVGSQVGRPGVLT  199
                    ||||||||||::  |||.|||||||::|||||||||:|||||.|  |||||
               151  NPVQIAADAAEAGIRGFSEQETTVGIARYAPFNALALLVGSQCGAPGVLT  200

200  QCSLEEATELKLGMLGHTCYAETISVYGTEPVFTDGDDTPWSKGFLASSY  249
                    |||:||||||.|||  |  |:||||:|||||.|||||||||||||||:||||.|
               201  QCSVEEATELELGMRGLTSYAETVSVYGTESVFTDGDDTPWSKAFLASAY  250

250  ASRGLKMRFTSGSGSEVQMGYAEGKSMLYLEARCIYITKAAGVQGLQNGS  299
                    |||||||:|||.|||.  |||.|:||||||.|||:|||:|||||||||.
               251  ASRGLKMRYTSGTGSEALMGYSESKSMLYLESRCIFITKGAGVQGLQNGA  300

300  VSCIGVPSAVPSGIRAVLAENLICSALDLECASSNDQTFTHSDMRRTARL  349
                    |||||:.:||||||||||||||||.|  ||||.||.|||||.|||:|||||
               301  VSCIGMTGAVPSGIRAVLAENLIASMLDLEVASANDQTFSHSDIRRTART  350

350  LMQFLPGTDFISSGYSAVPNYDNMFAGSNEDAEDFDDYNVIQRDLKVDGG  399
                    |||:||||||| |||||||||||||||| |||||||||::|||.||||
               351  LMQMLPGTDFIFSGYSAVPNYDNMFAGSNFDAEDFDDYNILQRDLMVDGG  400

400  LRPVREEDVIAIRNKAARALQAVFAGMGLPPITDEEVEAATYAHGSKDMP  449
                    ||||  ||:.|||||||||:||||  ::|||  |.||||:|||||||||||
               401  LRPVTEEETIAIRNKAARAIQAVFRELGLPLISDEEVDAATYAHGSKDMP  450

450  ERNIVEDIKFAQEIINKNRNGLEVVKALAKGGFPDVAQDMLNIQKAKLTG  499
                    .||:|||:  .:|::.:|  .||::|  ||..:||.|:|  ::||:  :.,:||
               451  ARNVVEDLAAVEEMMKRNITGLDIVGALSSSGFEDIASNILNMLRQRVTG  500

500  DYLHTSAIIVGEGQVLSAVNDVNDYAGPATGYRLQGERWEEIKNIPGALD  549
                    |||:||||:  :  :|:||||||:|||.||:||||  :|||.||||||:|.::
               501  DYLQTSAILDRQFDVVSAVNDINDYQGPGTGYRISAERWAEIKNIAGVVQ  550

550  PNELG*  555
                    |..::
               551  PGSIE*  556
```

FIG.3

\#  SEQ ID NO.: 5
\*  SEQ ID NO.: 6

FIG.4

```
dhaB_Kp.#  --->    1 ..............RAVLAENLIASMLDLEVASANDQTFSHSDIRRTART  36
                     ||||||||||||||||||||||||||||||||||||
dhaB_Cf.*  --->  301 VSCIGMTGAVPSGIRAVLAENLIASMLDLEVASANDQTFSHSDIRRTART 350

37 LMQMLPGTDFIFSGYSAVPNYDNMFAGSNFDAEDFDDYNILQRDLMVDGG  86
                     ||||||||||||||||||||||||||||||||||||||||||||||||||
                 351 LMQMLPGTDFIFSGYSAVPNYDNMFAGSNFDAEDFDDYNILQRDLMVDGG 400

87 LRPVTEAETIAIRQKAARAIQAVFRELGLPPIADEEVEAATYAQG.....  131
                     ||||||.||||||.||||||||||||||| |.||||:|||||:|
                 401 LRPVTEEETIAIRNKAARAIQAVFRELGLPLISDEEVDAATYAHGSKDMP 450
```

\#     SEQ ID No.: 7

\*     SEQ ID NO.: 8

FIG.5

PRODUCTION OF 1,3-PROPANEDIOL FROM GLYCEROL BY RECOMBINANT BACTERIA EXPRESSING RECOMBINANT DIOL DEHYDRATASE

This is a division of application Ser. No. 08/440,377, filed May 12, 1995 now U.S. Pat. No. 5,633,362.

FIELD OF INVENTION

This invention relates to a process for the bioconversion of glycerol to 1,3-propanediol by recombinant bacteria harboring a foreign gene encoding a diol dehydratase.

BACKGROUND 1,3-Propanediol is a monomer having potential utility in the production of polyester fibers and the manufacture of polyurethanes and cyclic compounds.

A variety of chemical routes to 1,3-propanediol are known. For example, 1,3-propanediol may be prepared from ethylene oxide and a catalyst in the presence of phosphine, water, carbon monoxide, hydrogen and an acid; by the catalytic solution phase hydration of acrolein followed by reduction; or from hydrocarbons such as glycerol, reacted in the presence of carbon monoxide and hydrogen over periodic table group VIII catalysts. Although it is possible to generate 1,3-propanediol by these methods, they are expensive and generate waste streams containing environmental pollutants.

Biological routes to 1,3-propanediol are known which utilize feedstocks produced from renewable resources. For example, bacterial strains able to convert glycerol into 1,3-propanediol are found e.g., in the species Klebsiella, Citrobacter, Clostridium, and Lactobacillus. In these bacteria, glycerol can enter either an oxidative or reductive pathway. Oxidation of glycerol results in the conversion of glycerol to dihydroxyacetone (DHA) by glycerol dehydrogenase and the DHA is phosphorylated by an adenosine triphosphate (ATP) dependent kinase to yield dihydroxyacetone phosphate (DHAP) which enters the glycolytic pathway in the cell. Reduction of glycerol is accomplished by an initial isomerization and dehydration catalyzed by glycerol dehydratase to yield 3-hydroxypropionaldehyde which is further reduced by 1,3-propanediol:NAD+ oxidoreductase to yield 1,3-propanediol, a dead end cellular metabolite. The expression of at least the first two enzymes involved in the oxidative pathway as well as the two enzymes involved in the reductive pathway in *K. pneumoniae* are coordinately regulated. The four enzyme system is functionally linked where the production of 1,3-propanediol from glycerol is dependent on the presence of the reductants supplied by the DHA to DHAP pathway.

The genes responsible for the conversion of glycerol to 1,3-propanediol have been isolated and are all encompassed by the dha regulon. In order to make use of the potential advantages of higher protein expression and growth rate of recombinant bacteria, several attempts have been made to express the dha regulon as heterologous genes in *E. coli*. For example, the dha regulon from Citrobacter (Daniel et al., *FEMS Microbiol. Lett.*, 100, 281, (1992)) and Klebsiella (Tong et al., *Appl. Environ. Microbiol.*, 57, 3541, (1991); have been expressed in *E. coli* and have been shown to convert glycerol to 1,3-propanediol. The expression of the dha regulon in recombinant bacteria offers potential advantages over wild type production of 1,3-propanediol. The genes involved in the dha regulon provide both the enzymes and the necessary reductants needed for the efficient conversion of glycerol to 1,3-propanediol. However, simultaneous overexpression of both glycerol dehydrogenase and glycerol dehydratase results in some of the glycerol being converted to DHA. It would be advantageous to convert all the glycerol to 1,3-propanediol by expressing only the reductive pathway enzymes while providing a different substrate for the generation of reductant. A preferred system would provide for a more efficient use of the glycerol substrate while maintaining high yields of diol product.

It has long been known that a number of bacteria are capable of using 1,2-propanediol as a sole carbon source. It is thought that this ability is conferred by a specific vitamin $B_{12}$ dependent diol dehydratase which is encoded by the pdu operon. The pdu operon is linked to the cob operon which encodes enzymes needed for the biosynthesis of vitamin $B_{12}$ and both operons are subject to the regulation of the same activator protein encoded by the c pocR gene.

Recently the genes encoding the diol dehydratase of *Klebsiella oxytoca* were cloned and sequenced and the genes were expressed in *E. coli*. Although active diol dehydratase was observed in these transformants, there is no evidence that these clones are able to metabolize a carbon substrate to 1,3-propanediol.

Various Salmonella and Klebsiella sp. are known to produce a diol dehydratase which catalyzes the conversion of 1,2-propanediol, under anaerobic conditions, to propionaldehyde and eventually to 1-propanol and propionic acid. The diol dehydratase has also been identified in Clostridia, and Propionibacterium but not in *E. coli*. The diol dehydratase from Klebsiella sp. can convert glycerol to 1,3-propanediol (Forage et al., Bacteriol, 149, 413 (1981)).

Although the primary function of the pdu diol dehydratase is in the metabolism of 1,2-propanediol, applicants have discovered that the expression of *K. pneumoniae* diol dehydratase in *E. coli* will catalyze the conversion of glycerol to 1,3-propanediol. The recombinant bacteria expressing the diol dehydratase pathway converts glycerol to the desired 1,3-propane- diol product and is not dependent on a linked system as with the glycerol dehydratase system. Applicants have discovered that transformation of recombinant bacteria with the pdu diol dehydratase genes from Klebsiella sp. affords a new, efficient and cost effective biological route to 1,3-propanediol.

SUMMARY OF THE INVENTION

Figure 5:
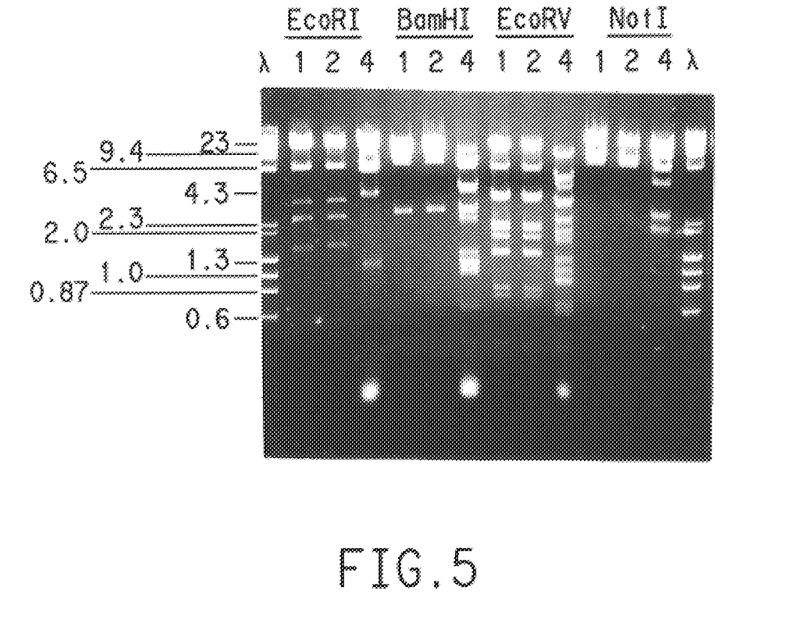
FIG. 5 depicts restriction digests (EcoR 1, BamH 1, EcoR V and Not1) of cosmids pKP1, pKP2 and pKP4, labeled as columns 1, 2 and 4 respectively, and separation on a 0.8% agarose gel electrophoresis. Molecular size markers were loaded on the lanes in the end. Columns labeled as number 4 represent the cosmid containing a diol dehydratase enzyme.

The present invention comprises a cosmid comprising a DNA fragment of about 35 kb isolated from *Klebsielia pneumoniae* wherein said fragment encodes an active diol dehydratase enzyme having the restriction digest in FIG. 5, columns numbered 4.

The present invention further comprises a transformed microorganism comprising a host micro-organism and the above-described cosmid.

The present invention further comprises a gene encoding an active diol dehydratase enzyme having the DNA sequence as listed in SEQ ID NO.:1 or a gene encoding an active alcohol dehydrogenase having the DNA sequence as listed in SEQ ID NO.:2.

The present invention further comprises a transformed microorganism comprising a host micro-organism and either of the above-described genes.

The present invention further comprises the bioconversion of a carbon substrate by transforming a microbial host with genes capable of expressing a diol dehydratase and contacting said transformed host with said substrate.

The present invention further comprises the bioconversion of a carbon substrate by transforming a microbial host with genes derived from a cosmid comprising a fragment of about 35 kb isolated from Klebsiella pneumoniae wherein said genes encode an active diol dehydratase enzyme and any other functional bacterial protein encoded by said cosmid, and contacting said transformed host with said substrate.

BRIEF DESCRIPTION OF THE FIGURES

FIG. 3 is a comparison of amino acid sequence coded by pduc gene of K. pneumoniae (SEQ ID NO.:5) with that of glycerol dehydratase from Citrobacter freundil (SEQ ID NO.:6) showing percent similarity and percent identity.

DETAILED DESCRIPTION OF THE INVENTION

As used herein the following terms may be used for interpretation of the claims and specification.

The term "construct" refers to a plasmid, virus, autonomously replicating sequence, phage or nucleotide sequence, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

The term "transformation" or "transfection" refers to the acquisition of new genes in a cell after the incorporation of nucleic acid.

The term "expression" refers to the transcription and translation to gene product from a gene coding for the sequence of the gene product. In the expression, a DNA chain coding for the sequence of gene product is first transcribed to a complimentary RNA which is often a messenger RNA and, then, the thus transcribed messenger RNA is translated into the above-mentioned gene product if the gene product is a protein.

The term "plasmid" or "vector" or "cosmid" as used herein refers to an extra chromosomal element often carrying genes which are not part of the central metabolism of the cell, and usually in the form of circular double-stranded DNA molecules.

The term "carbon substrate" means any carbon source capable of being metabolized by a microorganism wherein the substrate contains at least one carbon atom.

The term "dehydratase enzyme" will refer to any enzyme that is capable of converting a glycerol molecule to the product 3-hydroxypropionaldehyde. For the purposes of the present invention the dehydratase enzymes are either a glycerol dehydratase or a diol dehydratase having preferred substrates of glycerol and 1,2-propanediol, respectively.

The term "1,3-propanediol" refers to a compound of the formula $HOCH_2$—$CH_2$—$CH_2OH$, useful as a monomer in the production of polymers for fiber manufacture.

The following strains were deposited under the terms of the Budapest Treaty with the American Type Culture Collection (ATCC) (12301 Packlawn Drive, Rockville, Md. 20852, USA) : ATCC 69789 corresponds to E. coli DH5α containing cosmid pKP1. ATCC 69790 refers to E. coli DH5α a containing cosmid pKP4.

The present invention comprises a process for a biological production of 1,3-propanediol from glycerol using recombinant organisms. The process incorporates a transformed E. coli bacteria, transformed with a heterologous pdu diol dehydratase gene, having a specificity for 1,2-propanediol. The transformed E. coli is grown in the presence of glycerol as a carbon source and 1,3-propanediol is isolated from the growth media.

The process of the present invention provides a rapid, inexpensive and environmentally responsible source of 1,3-propanediol monomer useful in the production of polyesters and other polymers.

The invention provides a transformed host cell suitable for the expression of pdu diol dehydratase. Suitable host cells will generally be those that do not normally harbor a diol dehydratase gene. Preferred in the process of the present invention are E. coli, Bacillus subtilis, Bacillus licheniformis or Pichia pastoris. The diol dehydratase within the transformed host cell has been previously described by Toraya et al., J. Biol. Chem., 252, 963, (1977).

Isolation of Genes

The pdu diol dehydratase gene is obtained from any suitable source, but preferably from a bacteria known to be able to use 1,2-propanediol as a sole carbon source. Suitable bacteria known to harbor the pdu gene include but are not limited to Klebsiella sp., Clostridia sp., Salmonella sp., and Citrobacter sp.

Methods of obtaining desired genes from a bacterial genome are common and well known in the art of molecular biology. In the present invention virtually any method may be used to isolate the gene encoding the desired diol dehydratase. For example, if the sequence of the gene is known, suitable genomic libraries created by restriction endonuclease digestion may be screened with probes complementary to the desired gene sequence. Once the sequence is isolated, the DNA may be amplified using standard primer directed amplification methods such as polymerase chain reaction (PCR) (U.S. Pat. No. 4,683,202) to obtain amounts of DNA suitable for transformation using appropriate vectors.

Alternatively cosmid libraries may be created where large segments of genomic DNA (35–45 kb) may be packaged into vectors and used to transform appropriate hosts. Cosmid vectors are unique in being able to accommodate large quantities of DNA. Generally cosmid vectors have at least one copy of the cos DNA sequence which is needed for packaging and subsequent circularization of the foreign DNA. In addition to the cos sequence these vectors will also contain an origin of replication such as ColE1 and drug resistance markers such as a gene resistant to ampicillin or neomycin. A number of cosmid vectors are known in the art such as pJB8 (Ish-Horowicz et al., Nucl. Acids Res. 9, 2989 (1981)), containing an amp marker, ColE1 origin of replication and a singel cos site; and, c2RB (Bates et al., Gene, 26, 137, (1983)), containing 2 cos sites, both kanamycin and ampicillin resistance genes and the ColE1 origin of replication. Although any cosmid vector is suitable for use in the present invention the vector Supercos 1 provided by Stratagene (La Jolla, Calif.) is most preferred.

Typically, to clone cosmids, foreign DNA is isolated and ligated, using the appropriate restriction endonucleases, adjacent to the cos region of the cosmid vector. Cosmid vectors containing the linearized foreign DNA is then packaged in vitro in DNA packaging vehicle such as bacteriophage $\lambda$. During the packaging process the cos sites are cleaved and the foreign DNA is packaged into the head portion of the bacterial viral particle. These particles are then used to transfect suitable host cells such as E. coli. Once injected into the cell, the foreign DNA circularizes under the influence of the cos sticky ends. In this manner, large segments of foreign DNA can be introduced and expressed in recombinant host cells.

Cosmid vectors and cosmid transformation methods were used within the context of the present invention to clone large segments of genomic DNA from bacterial genera known to possess genes capable of processing glycerol to 1,3-propanediol. Specifically, genomic DNA from K. pneumoniae and K. aerogenes was isolated by methods well known in the art and digested with the restriction enzyme Sau3A for insertion into a cosmid vector Supercos 1 and packaged using GigapackII™ packaging extracts. Following construction of the vector E. coli XL1-Blue MR cells were transformed with the cosmid DNA. Transformants were screened for the ability to convert glycerol to 1,3-propanediol by growing the cells in the presence of glycerol and analyzing the media for 1,3-propanediol formation.

The DNA sequences generated from cosmid transformations named pKP4 and pKP5 were compared to DNA sequences in the Genbank data base. Several independent clones showing homology to pdu region of S. typhimurium were identified, suggesting that these transformants carried DNA encoding 1,2 propanediol utilizing enzymes including a 1,2-diol dehydratase gene. In contrast, in transformants named pKP1 and pKP2, an open reading frame showed extensive homology to the glycerol dehydratase gene from C. freundii, suggesting that these transformants containing DNA encoding the glycerol dehydratase gene.

Cells

The present invention further comprises a transformed host cell capable of converting a carbon substrate to 1,3-propanediol. As disclosed above, host cells may be transformed with a single gene, encoding the diol dehydratase, a series of specific genes encoding the diol dehydratase and other enzymes known to facilitate the process of bioconversion or with an entire cosmid DNA fragment. Preferred for use in the present invention is DH5α E. coli. However, it is contemplated that other cells will be amenable to transformation with the instant genes and will include, but are not limited to, other microorganisms such as Bacillus sp., Klebsiella sp., Citrobacter sp., Clostridia sp. and Pichia sp.

Carbon Substrate

The present invention provides a carbon substrate which is converted to the desired 1,3-propanediol end product via the enzymatic machinery of the transformed host organism. Virtually any carbon substrate that will serve as a substrate for a dehydratase enzyme is suitable for the present invention where alcohols are of greatest use. Preferred carbon substrates will include, but are not limited to, glycerol, ethylene-glycol, 1,2-propanediol, 1,2-butanediol, and 2,3-butanediol, wherein glycerol is most preferred.

Purification and Isolation of 1,3-propanediol

Methods for the purification of 1,3-propanediol from fermentation media are known in the art. For example propanediols can be obtained from cell media by subjecting the reaction mixture to extraction with an organic solvent, distillation and column chromatography (U.S. Pat. No. 5356812). A particularly good organic solvent for this process is cyclohexane (U.S. Pat. No. 5008473).

1,3-Propanediol may be identified directly by submitting the media to high pressure liquid chromatography (HPLC) analysis. Preferred in the present invention is a method where fermentation media is analyzed on an analytical ion exclusion column using a mobile phase of 0.01 N sulfuric acid in an isocratic fashion.

The following Examples are meant to illustrate the invention but are not intended to limit it in any way.

EXAMPLES

GENERAL METHODS

Restriction enzyme digestions, phosphorylations, ligations and transformations were done as described in Sambrook, J. et al., Molecular Cloning: A Laboratory Manual, Second Edition, Cold Spring Harbor Laboratory Press (1989). GeneClean (Stratagene, La Jolla, Calif.) was used to remove enzymes from restriction digests, as specified by the manufacturers. Restriction enzymes were obtained from New England Biolabs (Boston, Mass.) or Promega (Madison, Wis.) Growth media was obtained from GIBCO/BRL (Gaithersburg, Md.)

The meaning of abbreviations is as follows: "h" means hour(s), "min" means minute(s), "sec" means second(s), and "d" means day(s).

Media

Synthetic S12 medium was used in the screening of bacterial transformants for the ability to make 1,3-propanediol. S12 medium contains: ammonium sulfate, 10 mM; potassium phosphate buffer, pH 7.0, 50 mM; $MgCl_2$, 2 mM; $CaCl_2$, 0.7 mM; $MnCl_2$, 50 uM; $FeCl_3$, 1 uM; ZnCl, 1 uM; $CuSO_4$, 1.72 uM; $CoCl_2$, 2.53 uM; $Na_2MoO_4$, 2.42 uM; and thiamine hydrochloride, 2 uM.

Synthetic S15 medium was also used in the screening of bacterial transformants for the ability to make 1,3-propanediol. S15 medium contains: ammonium sulfate, 10 mM; potassium phosphate buffer, pH 7.0, 1 mM; MOPS/KOH buffer, pH 7.0, 50 mM; $MgCl_2$, 2 mM; $CaCl_2$, 0.7 mM; $MnCl_2$, 50 uM; $FeCl_3$, 1 uM; ZnCl, 1 uM; $Cuso_4$, 1.72 uM; $CoCl_2$, 2.53 uM; $Na_2MoO_4$, 2.42 uM; and thiamine hydrochloride, 2 uM.

Isolation and Identification 1.3-propanediol

The conversion of glycerol to 1,3-propanediol was monitored by HPLC. Analyses were performed using a Waters Maxima 820 HPLC system using UV (210 nm) and RI detection. Samples were injected onto a Shodex SH-1011 column (8 mm x300 mm, purchased from Waters, Milford, Mass.) equipped with a Shodex SH-1011P precolumn (6 mm x50 mm), temperature controlled at 50° C., using 0.01 N $H_2SO_4$ as mobile phase at a flow rate of 0.5 mL/min. When quantitative analysis was desired, samples were prepared with a known amount of trimethylacetic acid as external standard. Typically, the retention times of glycerol (RI detection), 1,3-propanediol (RI detection), and trimethylacetic acid (UV and RI detection) were 20.67 min, 26.08 min, and 35.03 min, respectively.

Production of 1,3-propanediol was confirmed by gas chromatography/mass spectrometry (GC/MS) with a Hewlett Packard 5890 Series II gas chromatograph coupled to a Hewlett Packard 5971 Series mass selective detector (EI) and a HP-INNOWax column (30 m length, 0.25 mm i.d., 0.25 micron film thickness). The retention time and mass spectrum of 1,3-propanediol generated from glycerol were compared to that of authentic 1,3-propanediol (m/e: 57, 58).

Cells

Host cells used for cosmid transformations were *E. coli* DH5α fully described in Jesse et al., *Focus*, 10, 69 (1988) and obtained from GIBCO/BRL.

Construction of K. pneumoniae and K. aerogenes cosmid libraries

*K. pneumoniae* (ATCC 25955) and *K. aerogenes* ((*K. pneumoniae* or *Aerobacter aerogenes*) ECL 2106) obtained from Dr. E.C.C. Lin, Harvard Medical School, Cambride, Mass., and described in Ruch, F.E. and Lin, E.C.C., Journal of Bacteriology, Vol. 124, p. 348 (Oct. 1975), were grown in 100 ml LB medium for 8 h at 37° C. with aeration. Bacteria (25 ml per tube) were centrifuged at 3,000 rpm for 15 min in a DuPont Sorvall GLC 2.B centrifuge at room temperature. The bacteria were pelleted and supernatant was decanted. The bacterial cell pellet was frozen at −20° C. The chromosomal DNA was isolated as outlined below with special care taken to avoid shearing of DNA (i.e., vortexing was avoided). One tube of bacteria was resuspended in 2.5 ml of 50 mM Tris-10 mM EDTA and 500 ul of lysozyme (1 mg/ml) was added. The pellet was gently resuspended and the suspension was incubated at 37° C. for 15 min. Sodium dodecyl sulfate was added to bring the final concentration to 0.5%. This resulted in the solution becoming clear. Proteinase K (50 ug/ml) was added and the suspension was incubated at 55° C. for 2 h. The tube was removed and transferred to an ice bath and sodium chloride was added to yield a 0.4 M final concentration. Two volumes of ethanol were added to the liquid. A glass tube was inserted to the interface and the DNA was gently spooled. DNA was dipped into a tube containing 70% ethanol. After drying in vacuo, the DNA was resuspended in 500 ul of water and the concentration of DNA was determined spectrophotometrically. A diluted aliquot of DNA was run on a 0.5% agarose gel to determine the intact nature of DNA.

The chromosomal DNA was partially digested with Sau3A as outlined by Sambrook et al., supra. DNA (2 ug) was digested with 2 units of Sau3A (Promega, Madison, Wis.) at room temperature in 200 ul of total volume. At 0, 5, 10 and 20 min, samples (50 ul) were removed and transferred to tubes containing 5 umol of EDTA. These tubes were incubated at 70° C. for 10 min. An aliquot (2 ul) was withdrawn and analyzed on a 0.5% agarose gel electrophoresis to determine the level of digestion and the rest of the sample (48 ul) was stored at −20° C. The gel was stained with ethidium bromide and visualized under UV to determine the partial digestion of the chromosomal DNA. A decrease in the size of the chromosomal DNA with increase in time was observed showing that the decrease in the size of the chromosomal DNA is due to the action of Sau3A. DNA was extracted from rest of the sample by standard protocol methods (Sambrook et al., supra).

A cosmid library of partially digested DNA from *K. pneumoniae* or *K. aerogenes* was prepared using Supercos cosmid vector kit and GigapackII™ packaging extracts using reagents purchased from Stratagene (La Jolla, Calif.). The instructions provided by the manufacturer were followed. The packaged *K. pneumoniae* contained $4 \times 10^4$ to $1.0 \times 10^5$ phage titer and the packaged *K. aerogenes* contained $1.2 \times 10^5$ phage per mL as determined by transfecting *E. coli* XL1-Blue MR.

Cosmid DNA was isolated from 6 of the *E. coli* transformants and found to contain large insert of DNA (25 to 30 kb).

EXAMPLE 1

Screening *E. coli* strains. transformed with a cosmid library DNA from *K. pneumoniae* and containing the glycerol dehydratase enzyme that produce 1.3- propanediol Example 1 demonstrated the screening of transformed *E. coli* cells with cosmid library DNA from *K. pneumoniae* for the presence of an enzyme that converted glycerol to 1,3-propanediol. Sequencing of two positive clones revealed that each contained a gene with a high degree of homology to the gene encoding glycerol dehydratase.

Six transformation plates containing approximately 1,000 colonies of *E. coli* XL1-Blue MR transfected with *K. pneumoniae* DNA were washed with 5 ml LB medium and centrifuged. The bacteria were pelleted and resuspended in 5 ml LB medium + glycerol. An aliquot (50 ul) was inoculated into a 15 ml tube containing S12 synthetic medium with 0.2% glycerol +400 ng per ml of vitamin $B_{12}$ +0.001% yeast extract +50 ug/ml ampicillin (50 amp). The tube was filled with the medium to the top, wrapped with parafilm and incubated at 30° C. A slight turbidity was observed after 48 h. Aliquots, analyzed for product distribution as described above at 78 h and 132 h, were positive for 1,3-propanediol, the later time points containing increased amounts of 1,3-propanediol.

The bacteria, testing positive for 1,3-propanediol production were plated onto a LB +50 amp, and serial dilutions were performed in order to isolate single colonies. Forty-eight single colonies were isolated and checked again for the production of 1,3-propane-diol. Cosmid DNA was isolated from 6 independent clones and transformed into *E. coli* strain DH5α. The transformants were again checked for the production of 1,3-propanediol. Two transformants were characterized further and designated as DH5α-pKP1 and DH5α-pKP2.

Figure 4:
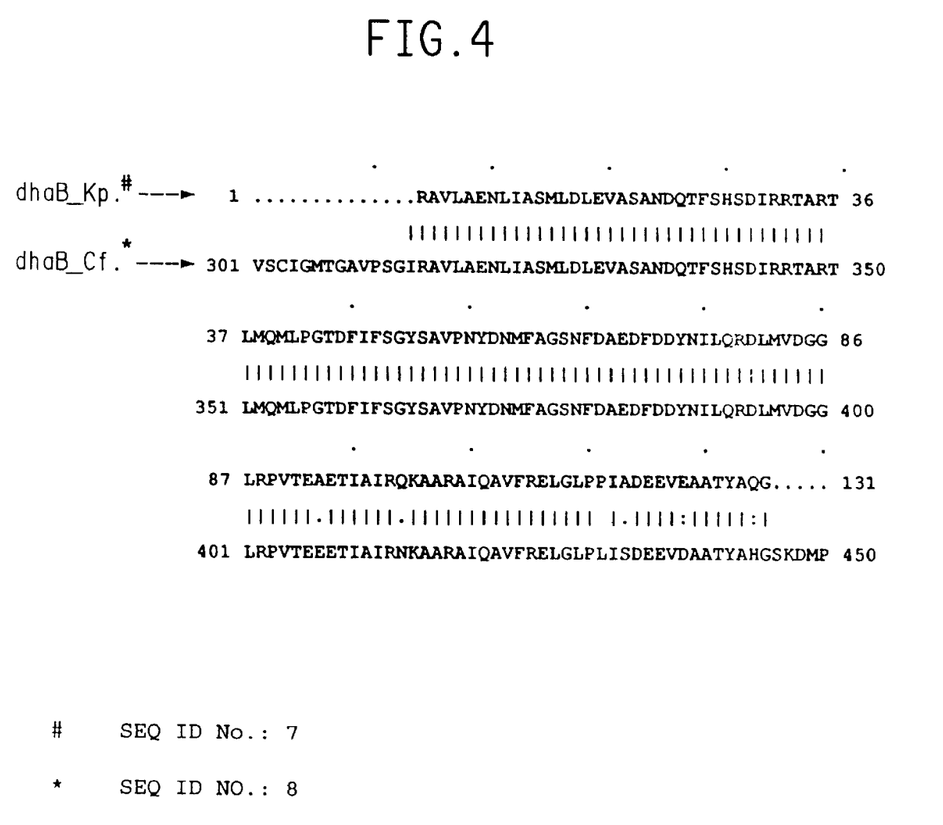
FIG. 4 is a comparison of the amino acid sequence deduced from an open reading frame of the glycerol dehydratase gene from K. pneumoniae (SEQ ID NO.:7) with the amino acid sequence encoded by the same gene from Citrobacter freundii (SEQ ID NO.:8). The figure shows the percent similarity and percent identity between the two deduced amino acid sequences.

DNA sequence analyses of DH5α-pKP1 and DH5α-pKP2 showed the presence of both glycerol dehydrogenase and glycerol dehydratase genes. Furthermore, the glycerol dehydratase gene of the transformed *E. coli* shared 96% similarity and 95% identity to the glycerol dehydratase gene from *Citrobacter freundii* (FIG. 4). Thus, pKP 1 and 2 appeared to contain the dha regulon genes from *K. pneumoniae*.

EXAMPLE 2

Screening *E. coli* strains, transformed with a cosmid library DNA from *K. pneumoniae* and containing the 1.2-propanediol dehydratase enzyme that produce 1,3-propanediol Example 2 demonstrated the screening of *E. coli* cells, transformed with cosmid library DNA from *K. pneumoniae*, for the presence of an active enzyme that enabled the conversion of glycerol to 1,3-propanediol. Sequencing of the positive clones revealed that each contained a gene with a high degree of homology to the gene encoding 1,2-propanediol dehydratase, encoded by the pdu operon.

Single colonies of E. coli XL1-Blue MR transfected with packaged cosmid DNA from K. pneumoniae were inoculated into microtiter wells containing 200 ul of S15 medium +0.2% glycerol +400 ng/ml of vitamin $B_{12}$ +0.001% yeast extract +50 ug/ml ampicillin (50 amp). In addition to the microtiter wells, a master plate containing LB +50 amp was also inoculated. After 96 h, 100 ul was withdrawn and centrifuged in a Rainin microfuge tube containing a 0.2 micron nylon membrane filter. Bacteria were retained and the filtrate was processed for HPLC analysis. Positive clones demonstrating 1,3-propanediol production were identified after screening approximately 240 colonies. Three positive clones were identified, two of which had grown on LB +50 amp and one of which had not. Single colonies were isolated from the two positive clones grown on LB +50 amp and verified for the production of 1,3-propanediol and designated as pKP4 and pKP5. Cosmid DNA was isolated from E. coli strains containing pKP4 and pKP5 and E. coli strain DH5α was transformed. Six independent transformants were verified for the production of 1,3-propanediol. E. coli strain DH5α containing pKP4 or pKP5 was able to convert glycerol to 1,3-propanediol as described below.

Production of 1.3-Propanediol with E. coli strains DH5α-pKP4 and DH5α-pKP5

A 2 mL screw capped cyrogenic vial, filled to capacity with media, was inoculated with E. coli strain DH5α a containing pKP4 or pKP5 and incubated at 30° C. The media was composed of S12 medium supplemented with 0.01% yeast extract, 0.008% casamino acids, 50 ug/mL ampicillin, 10 ug/mL kanamycin, 0.4 ug/mL vitamin $B_{12}$, and either 0.2% glycerol or 0.1% glycerol plus 0.1% D-glucose. Inoculation was performed directly from an agar plate culture (LB supplemented with 50 ug/mL ampicillin). After 66 hr, growth was determined by the absorbance at 600 nm ($OD_{600}$) and the extent of reaction and product distribution determined by HPLC. The results are presented in Table 1 and Table 2: the sample is identified by the transformant with a suffix notation indicating independent transformants, Gly is glycerol, Glu is D-glucose, Con. is conversion, Sel. is selectivity, Yld is yield, and NA is not applicable. Conversion, selectivity and yield were based on glycerol consumption.

TABLE 1

Production of 1,3-Propanediol from Glycerol

| Sample | $OD_{600}$ | [Gly] (mM) | [1,3-propanediol] (mM) | % Con. | % Sel. | % Yld. |
|---|---|---|---|---|---|---|
| media | NA | 23.0 | 0.0 | NA | NA | NA |
| pKP4-3 | 0.206 | 14.0 | 1.0 | 39 | 11 | 4 |
| pKP4-4 | 0.297 | 12.6 | 1.6 | 45 | 15 | 7 |
| pKP5-1 | 0.242 | 13.4 | 0.8 | 42 | 8 | 4 |
| pKP5-2 | 0.300 | 13.4 | 1.4 | 42 | 15 | 6 |

TABLE 2

Production of 1,3-Propanediol from Glycerol and Glucose

| Sample | $OD_{600}$ | [Gly] (mM) | [Glu] (mM) | [1,3-propanediol] (mM) | % Con. | % Sel. | % Yld. |
|---|---|---|---|---|---|---|---|
| media | NA | 10.7 | 4.3 | 0.0 | NA | NA | NA |
| pKP4-3 | 0.257 | 5.3 | 0.0 | 1.0 | 50 | 19 | 9 |
| pKP4-4 | 0.321 | 3.9 | 0.0 | 1.2 | 64 | 18 | 11 |
| pKP5-1 | 0.366 | 1.5 | 0.2 | 3.6 | 86 | 39 | 34 |
| pKP5-2 | 0.367 | 1.5 | 0.2 | 4.1 | 86 | 45 | 38 |

DNA sequence analysis of pKP4 and pKP5

The size of insert DNA in the case of both pKP4 and pKP5 varied from 25 to 30 Kb. Both clones had certain fragments that were common and certain fragments were different. A 22 kb EcoR1 fragment from pKP4 was eluted from an agarose gel using GeneClean and later digested with BamHI or EcoRV and the various fragments were subcloned into plasmid pIBI31 digested with EcoR1 or BamH1 or HinCII. Clones containing inserts were identified and DNA sequence was generated.

The DNA sequence that was generated showed homology to the cob and pocR and pdu genes of S. typhimurium. It is well known that the pdu operon in S. typhimurium codes for genes that are needed for 1,2-propanediol utilization. (Bobik et al., J. Bacteriol, 174, 2253 (1992)). Similarly, it is known that the cob operon encodes genes that are needed for vitamin $B_{12}$ synthesis. Within the pdu operon it is further recognized that the pduC gene encodes for diol dehydratase production.

Figure 1:
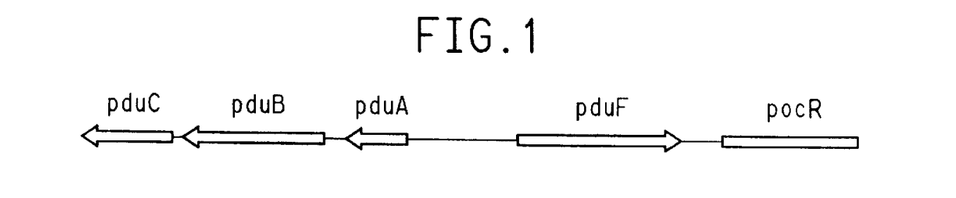
FIG. 1 is a schematic representation of the gene organization of pdu-cob region of K. pneumoniae. The DNA sequence was analyzed using the GCG-Wisconsin package and the open reading frames were compared to the S. typhimurium sequence using GAP. The percent identity and similarity are shown.

The region of K. pneumoniae coding for the pdu operon genes is shown in FIG. 1. FIG. 1 is a schematic representation of the gene organization of pdu-cob region of K. pneumoniae. Comparisons were made between this pdu-cob region and the same regions of the gene belonging to S. typhimurium using algorithms provided by Sequence Analysis Software of the University of Wisconsin (Genetics Computer Group, (1991), Version 7, April 1991, 575 Science Drive, Madison, Wis., USA 53711). A table giving the percent identity and similarity as calculated by the GAP program of the Genetics Computer Group are shown below.

| | Percent Similarity | | Percent Identity |
|---|---|---|---|
| pocR | 90.48% | | 84.35% |
| pduA | 100% | | 94.85% |
| pduB | 99.16% | | 96.64% |
| pduC | 98.31% | (partial seq.) | 94.92% |
| pduF | 92.42% | | 82.20% |

Figure 2:
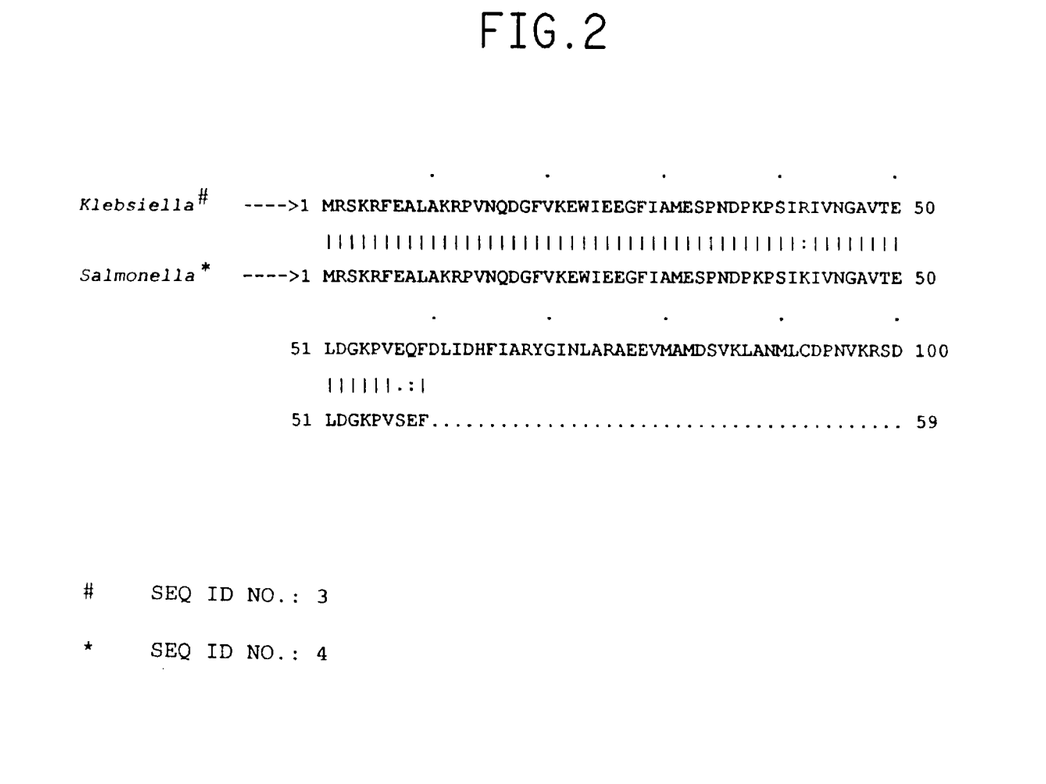
FIG. 2 is a comparison of the amino acid sequence encoded by the pduC gene of S. typhimurium (SEQ ID NO.:3) with the amino acid sequence encoded by the pduC gene of K. pneumoniae (SEQ ID NO.:4).

As can be seen by this comparison, and in FIG. 2, the pduC open reading frame showed extensive homology (98.31%) to the pduC gene of S. typhimurium. pduC was linked to pduF and showed homology to the gene encoding glycerol dehydratase from Citrobacter freundii (FIG. 3).

FIG. 3 is a comparison of the deduced amino acid sequence encoded by the pduC gene from K. pneumoniae (SEQ ID NO.:5) vs. the amino acid sequence encoded by the glycerol dehydratase gene of C. freundii (SEQ ID NO.:6). These comparisons showed that the percent similarity was only 84% and the identity only 70%. Thus, the pduC gene encoding for diol dehydratase was a clearly different enzyme and is being used to convert glycerol to 1,3-propanediol in these transformed E. coli strains. The sequence of the gene encoding this diol dehydratase enzyme is given in SEQ ID NO.:1.

Additionally, another open reading frame has been identified on the pdu gene which showed a high degree of homology with the regions encoding alcohol dehydrogenases. For example, deduced amino acid comparisons showed that this open reading frame had 43% homology with E. coli alcohol dehydrogenase and a 54% homology with the oxidoreductase of C. freundii. This open reading frame had been sequenced and is identified as SEQ ID NO.:2.

EXAMPLE 3

Screening E. coli strains, transformed with a cosmid library DNA from K. aerogenes and containing the glycerol dehydratase enzyme that produce 1,3-propanediol.

Example 3 demonstrated the screening of transformed E. coli cells with cosmid library DNA from K. aerogenes for the presence of an active enzyme that converted glycerol to 1,3-propanediol. Sequencing of the positive clones revealed that each contained a gene with a high degree of homology to the gene encoding 1,2-propanediol dehydratase, endcoded by the pdu operon.

Single colonies of E. coli XL1-Blue MR transfected with DNA from K. aerogenes were inoculated into microtiter wells containing 200 ul of S15 medium +0.2% glycerol +400 ng per ml of vitamin $B_{12}$ +0.001% yeast extract +50 ug/ml ampicillin (50 amp).

Culture supernatant was analyzed for the presence of 1,3-propanediol after 96 h. Two colonies were positive from 2 microtiter plates but after 1 week at room temperature the bacteria were not viable. A third mirotiter plate was inoculated and a master plate containing LB +50 amp was also inoculated. One positive clone labelled KAE3E10 was identified. The masterplate containing KAE3E10 used to replate the positive clone and cosmid DNA was isolated. DH5α cells were transformed with KAE3E10 DNA and transformants were screened for the conversion of glycerol to 1,3-propanediol. KAE3E10 was renamed pKA3 and contained an insert of approximately 40 kb. The DNA sequence of pKA3 showed a region that was homologous to cob and pocR and pdu operon of S. typhimurium.

Thus, it appeared that pKA3 also coded for a 1,2-propanediol utilizing operon. Diol dehydratase was presumably responsible for the conversion of glycerol to 1,3-propanediol.

What is claimed is:

1. A process for the bioconversion of a carbon substrate for diol dehydratase enzyme to the corresponding product comprising the steps of:
   (i) transforming a microbial host with genes encoding an enzymatically active bacterial diol dehydratase enzyme, the genes derived from
      (1) a cosmid, the cosmid comprising a DNA fragment of about 35 kb isolated from *Klebsiella pneumoniae* and contained within transformed *E. coli* deposited with the American Type Culture Collection under accession number ATCC 69790; or from
      (2) enzymatically active diol dehydratase genes isolated from the group consisting of members of the species Klebsiella sp., Clostridia sp., Salmonella sp. and Citrobacter sp, one subunit of the genes and having at least a 95% identity to the nucleic acid sequence of SEQ ID NO:1;
   (ii) contacting the transformed microbial host with the carbon substrate in a suitable medium; and
   (iii) recovering the corresponding product from the suitable medium.

2. The process of claim 1 wherein the carbon substrate is selected from the group consisting of ethylene glycol, 1,2-propanediol, glycerol and 2,3-butanediol.

3. The process of claim 2 wherein the carbon substrate is glycerol.

4. The process of claim 3 wherein the glycerol is converted to 1,3-propanediol.

5. The process of claim 1 wherein the microbial host is selected from the group consisting of members of the genera Eschericia, Bacillus, Klebsiella, Citrobacter, Saccharomyces, Clostridium and Pichia.

6. The process of claim 5 wherein the microbial host is selected from the group consisting of members of species *E. coli, Bacillus subtilis, Bacillus licheniformis* and *Pichia pastoris*.

7. The process of claim 6 wherein the microbial host is *E. coli*.

8. The process of claim 1 wherein (a) the transformed microbial host is recombinant *E. coli* DH5α containing a gene encoding an enzymatically active diol dehydratase enzyme, the gene comprising the DNA sequence of SEQ ID NO. 1; (b) the carbon substrate is glycerol; and (c) the product recovered in step (iii) is 1,3-propanediol.

9. A process for the bioconversion of glycerol to 1,3-propanediol comprising the steps of:
   (i) transforming a microbial host selected from the group consisting of the genera Eschericia, Bacillus, Klebsiella, Citrobacter, Saccharomyces, Clostridium and Pichia with genes encoding an enzymatically active bacterial diol dehydratase enzyme, the genes derived from a cosmid, the cosmid comprising a DNA fragment of about 35 kb isolated from *Klebsiella pneumoniae,* the cosmid contained within transformed *E. coli* deposited with the American Type Culture Collection under accession number ATCC 69790;
   (ii) contacting the transformed microbial host with carbon substrate in a suitable medium; and
   (iii) recovering 1,3-propanediol from a suitable medium.

10. The process of claims 8, 1 or 9 wherein the transformed microbial host further contains an alcohol dehydrogenase.

* * * * *

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 1665 base pairs
        ( B ) TYPE: nucleic acid
        ( C ) STRANDEDNESS: single
        ( D ) TOPOLOGY: linear     ( i i ) MOLECULE TYPE: DNA (genomic)

( i i i ) HYPOTHETICAL: NO

( x i ) SEQUENCE DESCRIPTION: SEQ ID NO:1:

```
ATGAGATCGA  AAAGATTTGA  AGCACTGGCG  AAACGCCCTG  TGAATCAGGA  TGGTTTCGTT      60
AAGGAGTGGA  TTGAAGAGGG  CTTTATCGCG  ATGGAAAGTC  CTAACGATCC  CAAACCTTCT     120
ATCCGCATCG  TCAACGGCGC  GGTGACCGAA  CTCGACGGTA  AACCGGTTGA  GCAGTTCGAC     180
CTGATTGACC  ACTTTATCGC  GCGCTACGGC  ATTAATCTCG  CCCGGGCCGA  AGAAGTGATG     240
GCCATGGATT  CGGTTAAGCT  CGCCAACATG  CTCTGCGACC  CGAACGTTAA  ACGCAGCGAC     300
ATCGTGCCGC  TCACTACCGC  GATGACCCCG  GCGAAAATCG  TGGAAGTGGT  GTCGCATATG     360
AACGTGGTCG  AGATGATGAT  GGCGATGCAA  AAAATGCGCG  CCCGCCGCAC  GCCGTCCCAG     420
CAGGCGCATG  TCACTAATAT  CAAAGATAAT  CCGGTACAGA  TTGCCGCCGA  CGCCGCTGAA     480
GGCGCATGGC  GCGGCTTTGA  CGAACAGGAG  ACCACCGTCG  CCGTGGCGCG  CTACGCGCCG     540
TTCAACGCCA  TCGCCCTGCT  GGTGGGTTCA  CAGGTTGGCC  GCCCCGGCGT  CCTCACCCAG     600
TGTTCGCTGG  AAGAAGCCAC  CGAGCTGAAA  CTGGGCATGC  TGGGCCACAC  CTGCTATGCC     660
GAAACCATTT  CGGTATACGG  TACGGAACCG  GTGTTTACCG  ATGGCGATGA  CACTCCATGG     720
TCGAAAGGCT  TCCTCGCCTC  CTCCTACGCC  TCGCGCGGCC  TGAAAATGCG  CTTTACCTCC     780
GGTTCCGGTT  CTGAAGTACA  GATGGGCTAT  GCCGAAGGCA  AATCGATGCT  TTATCTCGAA     840
```

-continued

| | | | | | | |
|---|---|---|---|---|---|---|
| GCGCGCTGCA | TCTACATCAC | CAAAGCCGCC | GGGGTGCAAG | GCCTGCAGAA | TGGCTCCGTC | 900 |
| AGCTGTATCG | GCGTACCGTC | CGCCGTGCCG | TCCGGGATCC | GCGCCGTACT | GGCGGAAAAC | 960 |
| CTGATCTGCT | CAGCGCTGGA | TCTGGAGTGC | GCCTCCAGCA | ACGATCAAAC | CTTTACCCAC | 1020 |
| TCGGATATGC | GGCGTACCGC | GCGTCTGCTG | ATGCAGTTCC | TGCCAGGCAC | CGACTTCATC | 1080 |
| TCCTCCGGTT | ACTCGGCGGT | GCCCAACTAC | GACAACATGT | CGCCGGTTC | CAACGAAGAT | 1140 |
| GCCGAAGACT | TCGATGACTA | CAACGTGATC | CAGCGCGACC | TGAAGGTCGA | TGGCGGCCTG | 1200 |
| CGGCCGGTGC | GTGAAGAGGA | CGTGATCGCC | ATTCGCAACA | AGCCGCCCG | CGCGCTGCAG | 1260 |
| GCGGTATTTG | CCGGCATGGG | TTTGCCGCCT | ATTACGGATG | AAGAGGTAGA | AGCCGCCACC | 1320 |
| TACGCCCACG | GTTCAAAAGA | TATGCCTGAG | CGCAATATCG | TCGAGGACAT | CAAGTTTGCT | 1380 |
| CAGGAGATCA | TCAACAAGAA | CCGCAACGGC | CTGGAGGTGG | TGAAAGCCCT | GGCGAAAGGC | 1440 |
| GGCTTCCCCG | ATGTCGCCCA | GGACATGCTC | AATATTCAGA | AAGCCAAGCT | CACCGGCGAC | 1500 |
| TACCTGCATA | CCTCCGCCAT | CATTGTTGGC | GAGGGCCAGG | TGCTCTCGGC | CGTGAATGAC | 1560 |
| GTGAACGATT | ATGCCGGTCC | GGCAACAGGC | TACCGCCTGC | AAGGCGAGCG | CTGGGAAGAG | 1620 |
| ATTAAAAATA | TCCCGGGCGC | GCTCGATCCC | AATGAACTTG | GCTAA | | 1665 |

(2) INFORMATION FOR SEQ ID NO:2:

(i) SEQUENCE CHARACTERISTICS:
        (A) LENGTH: 1335 base pairs
        (B) TYPE: nucleic acid
        (C) STRANDEDNESS: single
        (D) TOPOLOGY: linear     (ii) MOLECULE TYPE: DNA (genomic)

(iii) HYPOTHETICAL: NO

(xi) SEQUENCE DESCRIPTION: SEQ ID NO:2:

| | | | | | | |
|---|---|---|---|---|---|---|
| ATGCATACCT | TTTCTCTGCA | AACGCGCCTC | TACAGCGGCC | CGGGCAGCCT | GGCCGCGCTG | 60 |
| CAGCGCTTTA | GCCATCAGCA | CATCTGGATC | GTCTGCGACG | GCTTCCTGGC | GCGCTCGCCG | 120 |
| CTGCTTGACC | GACTGCGCGC | CGCGCTGCCC | GCCAGCAACC | GCGTCAGCGT | GTTCAGCGAT | 180 |
| ATTACACCGG | ATCCGACCAT | TCACACCGTG | GCGAAAGGGA | TAGCGCAGAT | GCAGGCCCTG | 240 |
| CGTCCGCAGG | TGGTGATCGG | CTTCGGCGG | GGCTCGGCGA | TGGATGCCGC | CAAGGCTATC | 300 |
| GTCTGGTTCA | GCCAGCAGGG | CGGTCTGCCT | GTTGACACCT | GCGTGGCGAT | CCCCACCACC | 360 |
| AGCGGTACCG | GTTCGGAAGT | GACCAGCGCC | TGCGTCATCA | GCGACCCGGA | AAAAGGGATC | 420 |
| AAGTACCCGC | TGTTCCATGA | GGCGCTCTGT | CCCGACATGG | CGATCATCGA | CCCGACGCTG | 480 |
| GTGGTTAGCG | TACCGCCCAC | CATCACAGCC | CATACCGGGC | TGGACGCGCT | GACCCACGCC | 540 |
| CTGGAGGCAT | GGGTCTCGCC | GCAGGCCACC | GATTTTACCG | ATGCGCTGGC | GGAAAAGGCC | 600 |
| GCCAGGCTGG | TGTTTCGCGC | CCTGCCCGTT | GCGATTCGTC | AGGGCGACTG | CATTGCGACC | 660 |
| CGCAGCAAAA | TGCACAATGC | ATCAACCCTC | GCCGGTATGG | CCTTTAGCCA | GGCTGGCCTT | 720 |
| GGGCTCAATC | ATGCGATCGC | CCATCAGCTT | GGCGGCCAGT | TCACCTCCC | CCATGGCCTG | 780 |
| GCCAATGCGC | TGCTGCTGAC | CGCGGTGATC | CGCTTCAATG | CCGGCGAGCC | GCGAGCGGCT | 840 |
| AAGCGCTATG | CACGCCTGGC | CAGGGCCTAC | CGCTTCTGCC | CGCCCGCAGC | TGGCGAACAG | 900 |
| GAGGCTTTCC | AGGCGCTGCT | TACCGCGGTG | GAAACGCTGA | ACAGCAGTG | CGCCATTCCC | 960 |
| CCCCTCAAGG | GCGCGCTGCA | GGAAAAGTAT | CCCCTTTTCT | TATCGCATCA | ACCAGTTCAA | 1020 |
| CATCATTGCT | CAGACGCACC | TGCCCGCACA | GCACGAAACC | GACCAGGTGG | CCGGCAATCA | 1080 |
| CCAGCGGGAT | GGAAAAATCG | GTTAACCCCG | CATGACAGCG | GTAGATACAC | AGCTGTCTTT | 1140 |

-continued

```
TTTCGAGGCT TCCAGCCCGC CGCAGCGGTC GCTCATGCGA CAGCGTCCGC TGTGCTCCGG    1200

GTGCTGACGC ATCAGCTGGC AAAACGGCGT GAAATTAAAC AATTCAGAAA TCTCATCACC    1260

GTGAATATTG ACGACCACAA CCGCCAGACT GGTGGCTTGC GCAAAATCCT GTGCGATTTT    1320

ATTGATGAGT TCTGA                                                     1335
```

( 2 ) INFORMATION FOR SEQ ID NO:3:

( i ) SEQUENCE CHARACTERISTICS:
        ( A ) LENGTH: 100 amino acids
        ( B ) TYPE: amino acid
        ( C ) STRANDEDNESS: unknown
        ( D ) TOPOLOGY: unknown     ( i i ) MOLECULE TYPE: peptide     ( i i i ) HYPOTHETICAL: NO     ( x i ) SEQUENCE DESCRIPTION: SEQ ID NO:3:

```
Met Arg Ser Lys Arg Phe Glu Ala Leu Ala Lys Arg Pro Val Asn Gln
 1           5                  10                  15

Asp Gly Phe Val Lys Glu Trp Ile Glu Glu Gly Phe Ile Ala Met Glu
            20                  25                  30

Ser Pro Asn Asp Pro Lys Pro Ser Ile Arg Ile Val Asn Gly Ala Val
            35                  40                  45

Thr Glu Leu Asp Gly Lys Pro Val Glu Gln Phe Asp Leu Ile Asp His
 50                  55                  60

Phe Ile Ala Arg Tyr Gly Ile Asn Leu Ala Arg Ala Glu Glu Val Met
 65                  70                  75                  80

Ala Met Asp Ser Val Lys Leu Ala Asn Met Leu Cys Asp Pro Asn Val
                85                  90                  95

Lys Arg Ser Asp
            100
```

( 2 ) INFORMATION FOR SEQ ID NO:4:

( i ) SEQUENCE CHARACTERISTICS:
        ( A ) LENGTH: 59 amino acids
        ( B ) TYPE: amino acid
        ( C ) STRANDEDNESS: unknown
        ( D ) TOPOLOGY: unknown     ( i i ) MOLECULE TYPE: peptide     ( i i i ) HYPOTHETICAL: NO     ( x i ) SEQUENCE DESCRIPTION: SEQ ID NO:4:

```
Met Arg Ser Lys Arg Phe Glu Ala Leu Ala Lys Arg Pro Val Asn Gln
 1           5                  10                  15

Asp Gly Phe Val Lys Glu Trp Ile Glu Glu Gly Phe Ile Ala Met Glu
            20                  25                  30

Ser Pro Asn Asp Pro Lys Pro Ser Ile Lys Ile Val Asn Gly Ala Val
            35                  40                  45

Thr Glu Leu Asp Gly Lys Pro Val Ser Glu Phe
 50                  55
```

( 2 ) INFORMATION FOR SEQ ID NO:5:

( i ) SEQUENCE CHARACTERISTICS:
        ( A ) LENGTH: 554 amino acids
        ( B ) TYPE: amino acid
        ( C ) STRANDEDNESS: unknown
        ( D ) TOPOLOGY: unknown ( i i ) MOLECULE TYPE: peptide ( i i i ) HYPOTHETICAL: NO ( x i ) SEQUENCE DESCRIPTION: SEQ ID NO:5:

```
Met Arg Ser Lys Arg Phe Glu Ala Leu Ala Lys Arg Pro Val Asn Gln
1               5                   10                  15
Asp Gly Phe Val Lys Glu Trp Ile Glu Gly Phe Ile Ala Met Glu
            20                  25                  30
Ser Pro Asn Asp Pro Lys Pro Ser Ile Arg Ile Val Asn Gly Ala Val
            35              40                  45
Thr Glu Leu Asp Gly Lys Pro Val Glu Gln Phe Asp Leu Ile Asp His
        50              55                  60
Phe Ile Ala Arg Tyr Gly Ile Asn Leu Ala Arg Ala Glu Glu Val Met
65              70                  75                  80
Ala Met Asp Ser Val Lys Leu Ala Asn Met Leu Cys Asp Pro Asn Val
                85                  90                  95
Lys Arg Ser Asp Ile Val Pro Leu Thr Thr Ala Met Thr Pro Ala Lys
            100                 105                 110
Ile Val Glu Val Val Ser His Met Asn Val Val Glu Met Met Met Ala
        115                 120                 125
Met Gln Lys Met Arg Ala Arg Arg Thr Pro Ser Gln Ala His Val
    130                 135                 140
Thr Asn Ile Lys Asp Asn Pro Val Gln Ile Ala Ala Asp Ala Ala Glu
145             150                 155                 160
Gly Ala Trp Arg Gly Phe Asp Glu Gln Glu Thr Thr Val Ala Val Ala
            165                 170                 175
Arg Tyr Ala Pro Phe Asn Ala Ile Ala Leu Leu Val Gly Ser Gln Val
            180                 185                 190
Gly Arg Pro Gly Val Leu Thr Gln Cys Ser Leu Glu Glu Ala Thr Glu
        195                 200                 205
Leu Lys Leu Gly Met Leu Gly His Thr Cys Tyr Ala Glu Thr Ile Ser
    210                 215                 220
Val Tyr Gly Thr Glu Pro Val Phe Thr Asp Gly Asp Asp Thr Pro Trp
225                 230                 235                 240
Ser Lys Gly Phe Leu Ala Ser Ser Tyr Ala Ser Arg Gly Leu Lys Met
            245                 250                 255
Arg Phe Thr Ser Gly Ser Gly Ser Glu Val Gln Met Gly Tyr Ala Glu
            260                 265                 270
Gly Lys Ser Met Leu Tyr Leu Glu Ala Arg Cys Ile Tyr Ile Thr Lys
        275                 280                 285
Ala Ala Gly Val Gln Gly Leu Gln Asn Gly Ser Val Ser Cys Ile Gly
    290                 295                 300
Val Pro Ser Ala Val Pro Ser Gly Ile Arg Ala Val Leu Ala Glu Asn
305                 310                 315                 320
Leu Ile Cys Ser Ala Leu Asp Leu Glu Cys Ala Ser Ser Asn Asp Gln
                325                 330                 335
Thr Phe Thr His Ser Asp Met Arg Arg Thr Ala Arg Leu Leu Met Gln
            340                 345                 350
Phe Leu Pro Gly Thr Asp Phe Ile Ser Ser Gly Tyr Ser Ala Val Pro
            355                 360                 365
Asn Tyr Asp Asn Met Phe Ala Gly Ser Asn Glu Asp Ala Glu Asp Phe
            370                 375                 380
```

Asp Asp Tyr Asn Val Ile Gln Arg Asp Leu Lys Val Asp Gly Gly Leu
385             390             395             400

Arg Pro Val Arg Glu Glu Asp Val Ile Ala Ile Arg Asn Lys Ala Ala
            405             410             415

Arg Ala Leu Gln Ala Val Phe Ala Gly Met Gly Leu Pro Pro Ile Thr
        420             425             430

Asp Glu Glu Val Glu Ala Ala Thr Tyr Ala His Gly Ser Lys Asp Met
        435             440             445

Pro Glu Arg Asn Ile Val Glu Asp Ile Lys Phe Ala Gln Glu Ile Ile
    450             455             460

Asn Lys Asn Arg Asn Gly Leu Glu Val Val Lys Ala Leu Ala Lys Gly
465             470             475             480

Gly Phe Pro Asp Val Ala Gln Asp Met Leu Asn Ile Gln Lys Ala Lys
            485             490             495

Leu Thr Gly Asp Tyr Leu His Thr Ser Ala Ile Ile Val Gly Glu Gly
            500             505             510

Gln Val Leu Ser Ala Val Asn Asp Val Asn Asp Tyr Ala Gly Pro Ala
        515             520             525

Thr Gly Tyr Arg Leu Gln Gly Glu Arg Trp Glu Glu Ile Lys Asn Ile
    530             535             540

Pro Gly Ala Leu Asp Pro Asn Glu Leu Gly
545             550

( 2 ) INFORMATION FOR SEQ ID NO:6:

( i ) SEQUENCE CHARACTERISTICS:
        ( A ) LENGTH: 555 amino acids
        ( B ) TYPE: amino acid
        ( C ) STRANDEDNESS: unknown
        ( D ) TOPOLOGY: unknown     ( i i ) MOLECULE TYPE: peptide     ( i i i ) HYPOTHETICAL: NO     ( x i ) SEQUENCE DESCRIPTION: SEQ ID NO:6:

Met Arg Arg Ser Lys Arg Phe Glu Val Leu Ala Gln Arg Pro Val Asn
1           5               10              15

Gln Asp Gly Leu Ile Gly Glu Trp Pro Glu Glu Gly Leu Ile Ala Met
        20              25              30

Glu Ser Pro Tyr Asp Pro Ala Ser Ser Val Lys Val Glu Asn Gly Arg
        35              40              45

Ile Val Glu Leu Asp Gly Lys Ser Arg Ala Glu Phe Asp Met Ile Asp
    50              55              60

Arg Phe Ile Ala Asp Tyr Ala Ile Asn Val Pro Glu Ala Glu Arg Ala
65              70              75              80

Met Gln Leu Asp Ala Leu Glu Ile Ala Arg Met Leu Val Asp Ile His
            85              90              95

Val Ser Arg Glu Glu Ile Ile Ala Ile Thr Thr Ala Ile Thr Pro Ala
            100             105             110

Lys Arg Leu Glu Val Met Ala Gln Met Asn Val Val Glu Met Met Met
        115             120             125

Ala Leu Gln Lys Met Arg Ala Arg Arg Thr Pro Ser Asn Gln Cys His
    130             135             140

Val Thr Asn Leu Lys Asp Asn Pro Val Gln Ile Ala Ala Asp Ala Ala
145             150             155             160

Glu Ala Gly Ile Arg Gly Phe Ser Glu Gln Glu Thr Thr Val Gly Ile
            165             170             175

-continued

```
Ala  Arg  Tyr  Ala  Pro  Phe  Asn  Ala  Leu  Ala  Leu  Leu  Val  Gly  Ser  Gln
               180                      185                     190

Cys  Gly  Ala  Pro  Gly  Val  Leu  Thr  Gln  Cys  Ser  Val  Glu  Glu  Ala  Thr
               195                      200                     205

Glu  Leu  Glu  Leu  Gly  Met  Arg  Gly  Leu  Thr  Ser  Tyr  Ala  Glu  Thr  Val
     210                           215                     220

Ser  Val  Tyr  Gly  Thr  Glu  Ser  Val  Phe  Thr  Asp  Gly  Asp  Asp  Thr  Pro
225                      230                     235                          240

Trp  Ser  Lys  Ala  Phe  Leu  Ala  Ser  Ala  Tyr  Ala  Ser  Arg  Gly  Leu  Lys
               245                      250                     255

Met  Arg  Tyr  Thr  Ser  Gly  Thr  Gly  Ser  Glu  Ala  Leu  Met  Gly  Tyr  Ser
               260                      265                     270

Glu  Ser  Lys  Ser  Met  Leu  Tyr  Leu  Glu  Ser  Arg  Cys  Ile  Phe  Ile  Thr
               275                      280                     285

Lys  Gly  Ala  Gly  Val  Gln  Gly  Leu  Gln  Asn  Gly  Ala  Val  Ser  Cys  Ile
          290                      295                     300

Gly  Met  Thr  Gly  Ala  Val  Pro  Ser  Gly  Ile  Arg  Ala  Val  Leu  Ala  Glu
305                           310                     315                     320

Asn  Leu  Ile  Ala  Ser  Met  Leu  Asp  Leu  Glu  Val  Ala  Ser  Ala  Asn  Asp
                    325                      330                     335

Gln  Thr  Phe  Ser  His  Ser  Asp  Ile  Arg  Arg  Thr  Ala  Arg  Thr  Leu  Met
               340                      345                     350

Gln  Met  Leu  Pro  Gly  Thr  Asp  Phe  Ile  Phe  Ser  Gly  Tyr  Ser  Ala  Val
               355                      360                     365

Pro  Asn  Tyr  Asp  Asn  Met  Phe  Ala  Gly  Ser  Asn  Phe  Asp  Ala  Glu  Asp
     370                           375                     380

Phe  Asp  Asp  Tyr  Asn  Ile  Leu  Gln  Arg  Asp  Leu  Met  Val  Asp  Gly  Gly
385                           390                     395                     400

Leu  Arg  Pro  Val  Thr  Glu  Glu  Thr  Ile  Ala  Ile  Arg  Asn  Lys  Ala
                    405                      410                     415

Ala  Arg  Ala  Ile  Gln  Ala  Val  Phe  Arg  Glu  Leu  Gly  Leu  Pro  Leu  Ile
               420                      425                     430

Ser  Asp  Glu  Glu  Val  Asp  Ala  Ala  Thr  Tyr  Ala  His  Gly  Ser  Lys  Asp
               435                      440                     445

Met  Pro  Ala  Arg  Asn  Val  Val  Glu  Asp  Leu  Ala  Ala  Val  Glu  Glu  Met
450                           455                     460

Met  Lys  Arg  Asn  Ile  Thr  Gly  Leu  Asp  Ile  Val  Gly  Ala  Leu  Ser  Ser
465                      470                     475                          480

Ser  Gly  Phe  Glu  Asp  Ile  Ala  Ser  Asn  Ile  Leu  Asn  Met  Leu  Arg  Gln
                    485                      490                     495

Arg  Val  Thr  Gly  Asp  Tyr  Leu  Gln  Thr  Ser  Ala  Ile  Leu  Asp  Arg  Gln
               500                      505                     510

Phe  Asp  Val  Val  Ser  Ala  Val  Asn  Asp  Ile  Asn  Asp  Tyr  Gln  Gly  Pro
          515                      520                     525

Gly  Thr  Gly  Tyr  Arg  Ile  Ser  Ala  Glu  Arg  Trp  Ala  Glu  Ile  Lys  Asn
     530                      535                     540

Ile  Ala  Gly  Val  Val  Gln  Pro  Gly  Ser  Ile  Glu
545                      550                     555
```

( 2 ) INFORMATION FOR SEQ ID NO:7:

( i ) SEQUENCE CHARACTERISTICS:
        ( A ) LENGTH: 131 amino acids
        ( B ) TYPE: amino acid
        ( C ) STRANDEDNESS: unknown (D) TOPOLOGY: unknown (ii) MOLECULE TYPE: peptide (iii) HYPOTHETICAL: NO (xi) SEQUENCE DESCRIPTION: SEQ ID NO:7:

```
Arg Ala Val Leu Ala Glu Asn Leu Ile Ala Ser Met Leu Asp Leu Glu
 1               5                  10                  15
Val Ala Ser Ala Asn Asp Gln Thr Phe Ser His Ser Asp Ile Arg Arg
                20                  25                  30
Thr Ala Arg Thr Leu Met Gln Met Leu Pro Gly Thr Asp Phe Ile Phe
             35                  40                  45
Ser Gly Tyr Ser Ala Val Pro Asn Tyr Asp Asn Met Phe Ala Gly Ser
     50                  55                  60
Asn Phe Asp Ala Glu Asp Phe Asp Asp Tyr Asn Ile Leu Gln Arg Asp
 65                  70                  75                  80
Leu Met Val Asp Gly Gly Leu Arg Pro Val Thr Glu Ala Glu Thr Ile
                 85                  90                  95
Ala Ile Arg Gln Lys Ala Ala Arg Ala Ile Gln Ala Val Phe Arg Glu
            100                 105                 110
Leu Gly Leu Pro Pro Ile Ala Asp Glu Glu Val Glu Ala Ala Thr Tyr
            115                 120                 125
Ala Gln Gly
        130
```

(2) INFORMATION FOR SEQ ID NO:8:

(i) SEQUENCE CHARACTERISTICS:
    (A) LENGTH: 150 amino acids
    (B) TYPE: amino acid
    (C) STRANDEDNESS: unknown
    (D) TOPOLOGY: unknown (ii) MOLECULE TYPE: peptide (iii) HYPOTHETICAL: NO (xi) SEQUENCE DESCRIPTION: SEQ ID NO:8:

```
Val Ser Cys Ile Gly Met Thr Gly Ala Val Pro Ser Gly Ile Arg Ala
 1               5                  10                  15
Val Leu Ala Glu Asn Leu Ile Ala Ser Met Leu Asp Leu Glu Val Ala
                20                  25                  30
Ser Ala Asn Asp Gln Thr Phe Ser His Ser Asp Ile Arg Arg Thr Ala
             35                  40                  45
Arg Thr Leu Met Gln Met Leu Pro Gly Thr Asp Phe Ile Phe Ser Gly
     50                  55                  60
Tyr Ser Ala Val Pro Asn Tyr Asp Asn Met Phe Ala Gly Ser Asn Phe
 65                  70                  75                  80
Asp Ala Glu Asp Phe Asp Asp Tyr Asn Ile Leu Gln Arg Asp Leu Met
                 85                  90                  95
Val Asp Gly Gly Leu Arg Pro Val Thr Glu Glu Glu Thr Ile Ala Ile
            100                 105                 110
Arg Asn Lys Ala Ala Arg Ala Ile Gln Ala Val Phe Arg Glu Leu Gly
            115                 120                 125
Leu Pro Leu Ile Ser Asp Glu Glu Val Asp Ala Ala Thr Tyr Ala His
    130                 135                 140
Gly Ser Lys Asp Met Pro
145                 150
```